(12) United States Patent
Onozawa et al.

(10) Patent No.: US 8,507,630 B2
(45) Date of Patent: Aug. 13, 2013

(54) ORGANIC INORGANIC COMPOSITE MATERIAL AND UTILIZATION THEREOF

(75) Inventors: Shun-ya Onozawa, Tsukuba (JP); Norihisa Fukaya, Tsukuba (JP); Kaori Saitou, Tsukuba (JP); Toshiyasu Sakakura, Tsukuba (JP); Hiroyuki Yasuda, Tsukuba (JP); Yukio Takagi, Numazu (JP); Masae Ueda, Tsukuba (JP)

(73) Assignees: National Institute of Advanced Industrial Science and Technology, Tokyo (JP); N.E. Chemcat Corporation, Tokyo (JP)

( * ) Notice: Subject to any disclaimer, the term of this patent is extended or adjusted under 35 U.S.C. 154(b) by 247 days.

(21) Appl. No.: 12/865,877

(22) PCT Filed: Mar. 5, 2009

(86) PCT No.: PCT/JP2009/054128
§ 371 (c)(1),
(2), (4) Date: Aug. 3, 2010

(87) PCT Pub. No.: WO2009/110531
PCT Pub. Date: Sep. 11, 2009

(65) Prior Publication Data
US 2011/0004010 A1    Jan. 6, 2011

(30) Foreign Application Priority Data

Mar. 7, 2008    (JP) ................................. 2008-057594

(51) Int. Cl.
*C08L 83/04*    (2006.01)
*C09D 183/04*    (2006.01)

(52) U.S. Cl.
USPC .......................................... 528/15; 428/447

(58) Field of Classification Search
USPC .......................................... 528/15; 428/447
See application file for complete search history.

(56) References Cited

U.S. PATENT DOCUMENTS
2005/0191503 A1    9/2005 Jones

FOREIGN PATENT DOCUMENTS

| BE | 1014952 A3 | 7/2004 |
|----|------------|--------|
| JP | 2003 313024 | 11/2003 |
| JP | 2004 175793 | 6/2004 |
| JP | 2005 60335 | 3/2005 |
| JP | 2005 247682 | 9/2005 |
| JP | 2005 255581 | 9/2005 |
| JP | 2007 537055 | 12/2007 |
| WO | WO 00/02656 | 1/2000 |
| WO | WO 2005/086652 A2 | 9/2005 |

OTHER PUBLICATIONS

Shinji et al. (JP 2004-175793, English machine translation).*
Miyaura, Norio et al., "A New Stereospecific Cross-Coupling By The Palladium-Catalyzed Reaction Of 1-Alkenylboranes With 1-Alkenyl Or 1-Alkynyl Halides", Tetrahedron Letters, No. 36, pp. 3437-3440, (1979).
Miyashita, A. et al., "2,2'-Bis(Diphenylphosphino)-1,1'-Binaphthyl (BINAP), A New Atropisomeric Bis(Triaryl)Phosphine, Synthesis And Its Use In The Rh(I)-Catalyzed Asymmetric Hydrogenation Of α-(Acylamino)Acrylic Acids", Tetrahedron, vol. 40, No. 8, pp. 1245-1253, (1984).
Extended European Search Report issued Jun. 8, 2012, in Patent Application No. 09717502.0.
Ralf A. Findeis, et al., "Tripodal Phosphane Ligands with Novel Linker Units and Their Rhodium Complexes as Building Blocks for Dendrimer Catalysts", European Journal of Inorganic Chemistry, XP 55028412, Jan. 2003, pp. 99-110.
Office Action issued Mar. 6, 2013, in European patent application No. 09717502.0.

* cited by examiner

*Primary Examiner* — Robert Havlin
(74) *Attorney, Agent, or Firm* — Oblon, Spivak, McClelland, Maier & Neustadt, L.L.P.

(57) ABSTRACT

The invention has an object to obtain an organic inorganic composite material having high activity and high selectivity, and suitable as a catalyst material having small elution of an active metal from a carrier, and further to obtain an organosilicon compound suitable for the preparation of the composite material. The composite material is an organic inorganic composite material comprising an organosilicon compound having at least two groups containing reactive silicon at a molecular end, bonded to one silicon atom constituting the organosilicon compound, and an inorganic oxide material, the organosilicon compound and the inorganic oxide material being bonded to each other through a plurality of groups containing reactive silicon of the organosilicon compound. The organosilicon compound is represented by the following general formula (1) or (2).

6 Claims, 1 Drawing Sheet

US 8,507,630 B2

ORGANIC INORGANIC COMPOSITE MATERIAL AND UTILIZATION THEREOF

TECHNICAL FIELD

The present invention relates to a novel organic inorganic composite material. In more detail, the invention relates to a catalyst comprising the organic inorganic composite material and a transition metal compound, a catalytic reaction using the catalyst, and an organosilicon compound useful in preparation of the organic inorganic composite material.

BACKGROUND ART

A method of bonding an organic modifying group to an inorganic oxide material such as silica gel or zeolite to form an organic inorganic composite material, thus changing chemical and physical properties of the inorganic oxide material, has conventionally be conducted.

The organic inorganic composite material thus obtained has been used in, for example, industrial materials such as various adsorbents, columns and surfactants; pharmaceutical materials such as drug delivery system, biological affinity materials and test chips; and electronic materials such as sensors, organic EL and liquid crystals.

It is generally desired in the organic inorganic composite material that a bond between an organic material (organic group) and an inorganic oxide material (carrier) is strong. In particular, in the case that an organic inorganic composite material is used as a catalyst material, there is the advantage that a strong bond between an organic group constituting an organic inorganic composite material and a carrier suppresses elution (leaching) of catalyst active species, and maintains high-state catalyst activity.

Hitherto, an organic inorganic composite material comprising an organic material and an inorganic oxide material, fixed with a covalent bond at only one place has been known as an organic inorganic composite material used as a catalyst material (Patent Document 1). However, such a covalent bond at only one place was not sufficient for fixation.

It is well known that a catalyst material is used in various chemical reactions. For example, a coupling reaction such as Suzuki-Miyaura coupling reaction using a catalyst, a hydrogenation reaction and the like are very important reactions in synthesis of pharmaceutical and agricultural products and electronic materials. A homogeneous catalyst such as palladium or rhodium has been used as a catalyst in those reactions (Non-Patent Documents 1 and 2).

However, such a homogeneous catalyst has high activity and selectivity, but is difficult to be separated from a product after reaction. This led to the decrease in performance of a product and high cost due to such catalyst being unable to be recycled.

To solve those problems, in recent years heterogeneous catalysts comprising a homogeneous catalyst fixed to various resins have been studied (Patent Document 2). In addition to those technologies, investigations have been made in which an organic group is fixed to silica and other oxides, and an active metal is further coordinated thereto, thereby forming a catalyst (Patent Document 3).

However, in the case that a resin is used as a carrier, there was the problem in durability that a catalyst is deactivated by swelling or the like of a resin, depending on the kind of an organic solvent and a reaction temperature. Furthermore, in the case that an oxide is used as a carrier, a bond between the oxide and an organic group is not strong, leading to the problem that a catalyst component elutes in a reaction liquid. Thus, there was a problem of the decrease in performance of an objective product due to the problem.

Patent Document 1: JP-A 2004-175793
Patent Document 2: JP-A 2005-60335
Patent Document 3: JP-A 2005-255581
Non-Patent Document 1: Tetrahedron Letter, 36, 3437 (1979)
Non-Patent Document 2: Tetrahedron, 40, 1245 (1984)

DISCLOSURE OF THE INVENTION

Problems that the Invention is to Solve

Accordingly, an object of the present invention is to obtain an organic inorganic composite material having high activity and selectivity, and suitable for a catalyst material having small elution of an active metal from a carrier, and to obtain an organosilicon compound suitable for production of such an organic inorganic composite material.

Means for Solving the Problems

As a result of intensive investigations to solve the above problems, the present inventors have found that an organic inorganic composite material can be obtained by comprising an organosilicon compound and an inorganic oxide material, strongly fixed to each other by bonding the organosilicon compound and the inorganic oxide material, constituting the organic inorganic composite material through a plurality of bonding points. They have further found that an excellent organic inorganic composite catalyst is obtained by synthesizing an organosilicon compound capable of being bonded to an inorganic oxide material at a plurality of bonding points, and supporting catalyst active species such as a noble metal to an organic inorganic composite material obtained by bonding the organosilicon compound and an inorganic oxide carrier, by a means such as coordination, and have completed the present invention based on this finding.

Specifically, the present invention provides an organic inorganic composite material comprising an organosilicon compound having at least two groups containing reactive silicon at a molecular end, bonded to one silicon atom constituting the organosilicon compound, and an inorganic oxide material, the organosilicon compound and the inorganic oxide material being bonded to each other through a plurality of groups containing reactive silicon of the organosilicon compound.

The present invention further provides an organic inorganic composite catalyst comprising the organic inorganic composite material having supported thereon a transition metal or a compound thereof.

The present invention further provides a catalyst for cross-coupling reaction containing the organic inorganic composite material and a transition metal or a compound thereof, a coupling reaction method utilizing the catalyst, and a reaction synthetic product obtained by the method.

The present invention further provides a catalyst for hydrogenation reaction containing the organic inorganic composite material and a transition metal or a compound thereof, a hydrogenation reaction method utilizing the catalyst, and a reaction synthetic product obtained by the method.

The present invention further provides an organosilicon compound represented by the following general formula (1):

(1)

wherein X represents chlorine, bromine, iodine, siloxy group, hydroxy group, alkoxy group, allyl group or imidazolyl group, Y represents a monovalent organic group containing at least one of hydroxyl group, alkoxy group, aryloxy group, isocyanato group, mercapto group, phosphino group, amino group, imino group, halogen and heterocyclic ring, A represents a divalent hydrocarbon group, R represents methyl group, ethyl group, butyl group or phenyl group, Q represents methyl group, ethyl group, butyl group or phenyl group, k is an integer of 1 to 3, n is 1 or 2, m is 2 or 3, l is 0 or 1, and l+m+n is 4, or the following general formula (2):

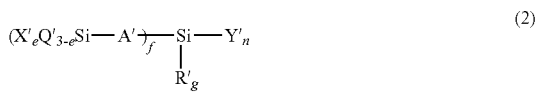

(2)

wherein X' represents chlorine, bromine, iodine, siloxy group, hydroxy group, alkoxy group, allyl group or imidazolyl group, Y' represents a monovalent organic group containing halogen, A' represents a divalent hydrocarbon group, R' represents methyl group, ethyl group, butyl group or phenyl group, Q' represents methyl group, ethyl group, butyl group or phenyl group, e is an integer of 1 to 3, f is 2 or 3, h is 1 or 2, g is 0 or 1, and f+h+g is 4, and a precursor of the organosilicon compound.

Effect of the Invention

According to the present invention, an organic inorganic composite material comprising an organosilicon compound and an inorganic oxide material, strongly bonded to each other is obtained by bonding the organosilicon compound and the inorganic oxide material, constituting the organic inorganic composite material at a plurality of bonding points.

Therefore, when a transition metal compound containing catalyst active species such as a noble metal is supported on the organic inorganic composite material by a means such as coordination, an organic inorganic composite catalyst exhibiting excellent anti-leaching performance can be obtained.

By using the organic inorganic composite catalyst in various catalytic reactions, the objective product can be obtained with good yield, and residual heavy metal in the product can be reduced. Furthermore, the organic inorganic composite catalyst can easily be isolated from a reaction liquid, and can therefore be repeatedly used in a reaction, which is economical.

BEST MODE FOR CARRYING OUT THE INVENTION

The organic inorganic composite material of the present invention (hereinafter referred to as a "composite material of the invention") is obtained by bonding an organosilicon compound having at least two groups containing reactive silicon at a molecular end, bonded to one silicon atom constituting the organosilicon compound, and an inorganic oxide material through a silicon atom of the group containing reactive silicon, and preferably by covalent-bonding an oxygen atom of the inorganic oxide material and a silicon atom of the group containing reactive silicon.

The organosilicon compound which is one raw material of the composite material of the invention is that at least two groups containing reactive silicon at a molecular end are bonded to one silicon atom constituting the organosilicon compound. A group other than the group containing reactive silicon at a molecular end and bonded to one silicon atom is not particularly limited so long as it does not impair a bond between the inorganic oxide material and the reactive silicon, and examples of the group include a monovalent hydrocarbon group, and a substituent having an ability to support transition metal or a compound thereof. The silicon compound is preferably a compound in which three groups containing reactive silicon at a molecular end are bonded to one silicon atom, and one substituent having an ability to support a transition metal or a compound thereof at a molecular end is bonded to the same silicon atom.

The group containing reactive silicon at a molecular end is a group bonding to an inorganic oxide material and the like, and includes a group represented by the following general formula (3):

(3)

wherein X" represents chlorine, bromine, iodine, siloxy group, hydroxy group, alkoxy group, allyl group or imidazolyl group, and preferably chlorine, alkoxy group, allyl group or imidazolyl group. The alkoxy group of X" is preferred to be an alkoxy group having 1 to 10 carbon number, such as methoxy group, ethoxy group, propoxy group, isopropoxy group or t-butoxy group. Q" represents methyl group, ethyl group, butyl group or phenyl group, and preferably methyl group from the standpoint of easy synthesis and availability of raw materials. A" is a divalent hydrocarbon group, preferably a linear alkylene group having 2 or more carbon number, and particularly preferably propylene group. d is an integer of 1 to 3.

The substituent having an ability to support a transition metal or a compound thereof includes substituents containing a hetero atom having an ability to coordinate to a transition metal. Specific examples of the substituent include a monovalent organic group having at an end thereof at least one of hydroxyl group, alkoxy group, aryloxy group, isocyanato group, mercapto group, phosphino group, amino group, imino group, halogen and heterocyclic ring. The monovalent organic group may further contain other hetero elements and metal elements in the skeleton.

Of the above substituents, the monovalent organic group containing alkoxy group and aryloxy group is preferably an organic group comprising alkylene group having 1 to 10 carbon number and preferably 1 to 3 carbon number, having bonded thereto alkoxy group and aryloxy group. Specific examples of the alkoxy group include methoxy group, ethoxy group, propoxy group, isopropoxy group, t-butoxy group, hexyloxy group, cyclohexyloxy group, benzyloxy group, methoxyethoxy group, methoxymethoxy group and tetrahydropyranyloxy group. Specific examples of the aryloxy group include phenoxy group, naphthyloxy group and tolyloxy group.

Of the above substituents, a monovalent organic group containing mercapto group and phosphino group is preferably an alkylene group having 1 to 10 carbon number and preferably 1 to 3 carbon number, having bonded thereto an unsubstituted or substituted mercapto group and phosphino group. Examples of the substituted mercapto group include methylthio group and phenylthio group. Specific examples of the phosphino group include dimethylphosphino group, dibutylphosphino group, dicyclohexylphosphino group and diphenylphosphino group.

Of the above substituents, a monovalent organic group containing amino group and imino group is preferably an alkylene group having 1 to 10 carbon number and preferably 1 to 3 carbon number, having bonded thereto amino group and imino group. The amino group is preferably an amino group such as tertiary amino group, in which at least one hydrogen atom is substituted with hydrocarbon group, and specific examples thereof include methylamino group, ethylamino group, phenylamino group, dimethylamino group, diethylamino group, methylethylamino group, phenylmethylamino group, phenylethylamino group and diphenylamino group. Specific examples of the imino group include methylimino group, benzylimino group and phenylimino group.

Of the above substituents, a monovalent organic group containing a halogen is preferably an alkylene group having 1 to 10 carbon number and preferably 1 to 3 carbon number, having bonded thereto a halogen such as chlorine or bromine. Specific examples of the monovalent organic group containing a halogen include chloromethyl group, chloroethyl group, chloropropyl group, bromomethyl group, bromoethyl group and bromopropyl group.

Of the above substitutents, a monovalent organic group containing a heterocyclic ring is preferably an alkylene group having 1 to 10 carbon number and preferably 1 to 3 carbon number, having bonded thereto a heterocyclic ring such as pyridyl group, pyrrolyl group, furyl group, thienyl group, epoxy group, piperidyl group, morpholyl group, cyclic imino group, oxazolyl group or thiazolyl group.

Of the above substituents, an alkylene group having 1 to 3 carbon number, having bonded thereto isocyanato group, mercapto group, methylthio group, phenylthio group, dimethylphosphino group, dibutylphosphino group, dicyclohexylphosphino group, diphenylphosphino group, dimethylamino group, epoxy group, oxazolyl group, chlorine or bromine is preferred from the standpoint of coordination ability to a transition metal, reactivity and the like.

On the other hand, examples of the monovalent hydrocarbon group include methyl group, ethyl group, butyl group and phenyl group, and methyl group is desired due to its ease of synthesis and ease of availability of a raw material.

Specifically, the organosilicon compound becoming a raw material of the composite material of the invention includes a compound represented by the following general formula (1) or (2):

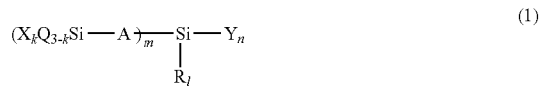
(1)

In the above formula (1), X represents chlorine, bromine, iodine, siloxy group, hydroxy group, alkoxy group, allyl group or imidazolyl group, and preferably chlorine, alkoxy group allyl group or imidazolyl group. Y represents a monovalent organic group containing at least one of hydroxyl group, alkoxy group, aryloxy group, isocyanato group, mercapto group, phosphino group, amino group, imino group and heterocyclic ring, and preferably phosphino group and amino group. A represents a divalent hydrocarbon group, and preferably propylene group. R represents methyl group, ethyl group, butyl group or phenyl group, and preferably methyl group. Q represents methyl group, ethyl group, butyl group or phenyl group, and preferably methyl group. k is an integer of 1 to 3, n is 1 or 2, m is 2 or 3, l is 0 or 1, and l+m+n is 4. Preferably, k is 1, n is 1, m is 3 and l is 0.

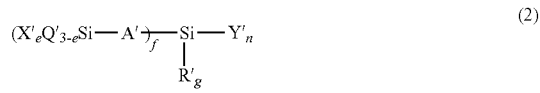
(2)

In the above formula (2), X' represents chlorine, bromine, iodine, siloxy group, hydroxy group, alkoxy group, allyl group or imidazolyl group, and preferably alkoxy group or imidazolyl group. Y' represents a monovalent organic group containing a halogen, and preferably chloropropyl group or bromopropyl group. A' represents a divalent hydrocarbon group, and preferably propylene group. R' represents methyl group, ethyl group, butyl group or phenyl group, and preferably methyl group. Q' represents methyl group, ethyl group, butyl group or phenyl group, and preferably methyl group. e is an integer of 1 to 3, f is 2 or 3, h is 1 or 2, g is 0 or 1, and f+h+g is 4. Preferably, f is 3, e is 1, h is 1 and g is 0.

Further specific examples of the organosilicon compound are shown below.

TABLE 1

| No. | Organosilicon compound |
|---|---|
| 1-1 | |
| 1-2 | |

TABLE 1-continued

| No. | Organosilicon compound |
|---|---|
| 1-3 | (structure) |
| 1-4 | (structure) |
| 1-5 | (structure) |
| 1-6 | (structure) |
| 1-7 | (structure) |
| 1-8 | (structure) |

TABLE 1-continued
| No. | Organosilicon compound |
|---|---|
| 1-9 | 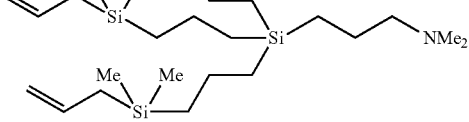 |
| 1-10 |  |
| 1-11 |  |
| 1-12 |  |
| 1-13 |  |
| 1-14 |  |

TABLE 1-continued

| No. | Organosilicon compound |
|---|---|
| 1-15 | |
| 1-16 | |
| 1-17 | |
| 1-18 | |
| 1-19 | |
| 1-20 | |

TABLE 1-continued

| No. | Organosilicon compound |
|---|---|
| 1-21 | (structure) |
| 1-22 | (structure) |
| 1-23 | (structure) |
| 1-24 | (structure) |
| 1-25 | (structure) |
| 1-26 | (structure) |
| 1-27 | (structure) |

TABLE 1-continued
| No. | Organosilicon compound |
|---|---|
| 1-28 | 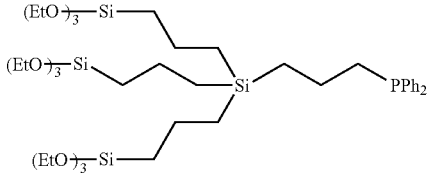 |
| 1-29 | 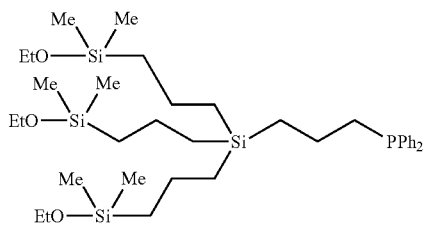 |
| 1-30 | 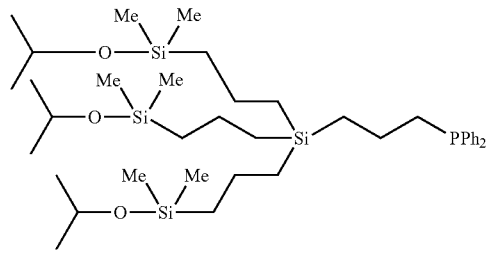 |
| 1-31 | 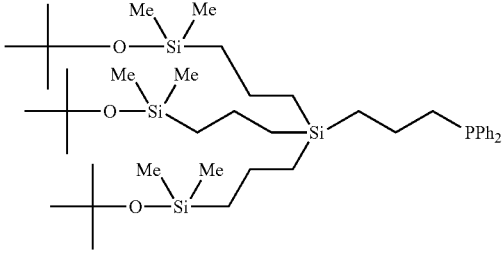 |
| 1-32 | 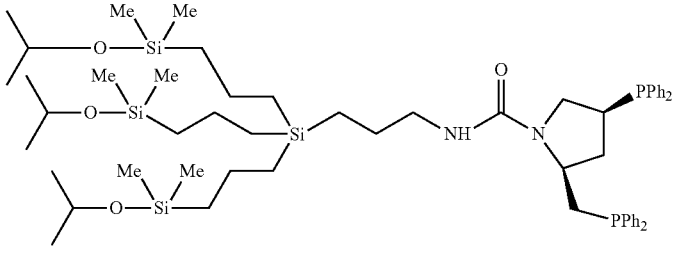 |
| 1-33 | 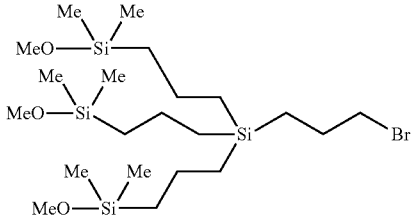 |

TABLE 1-continued

| No. | Organosilicon compound |
|---|---|
| 1-34 | (MeO-Si(Me)₂-CH₂CH₂CH₂-)₃Si-CH₂CH₂CH₂-Cl |
| 1-35 | (EtO-Si(Me)₂-CH₂CH₂CH₂-)₃Si-CH₂CH₂CH₂-Br |
| 1-36 | (EtO-Si(Me)₂-CH₂CH₂CH₂-)₃Si-CH₂CH₂CH₂-Cl |
| 1-37 | (PrO-Si(Me)₂-CH₂CH₂CH₂-)₃Si-CH₂CH₂CH₂-Br |
| 1-38 | (PrO-Si(Me)₂-CH₂CH₂CH₂-)₃Si-CH₂CH₂CH₂-Cl |
| 1-39 | (iPrO-Si(Me)₂-CH₂CH₂CH₂-)₃Si-CH₂CH₂CH₂-Br |

TABLE 1-continued
| No. | Organosilicon compound |
|---|---|
| 1-40 | 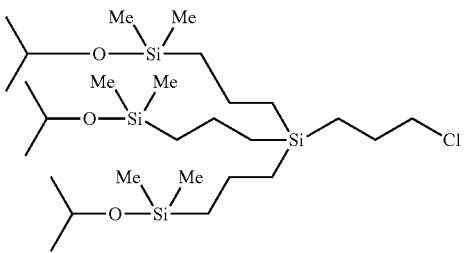 [SMILES: CC(C)O[Si](C)(C)CCC[Si](CCCCl)(CCC[Si](C)(C)OC(C)C)CCC[Si](C)(C)OC(C)C] |
| 1-41 | 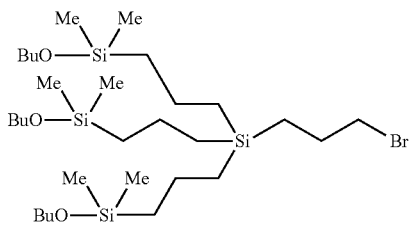 |
| 1-42 | 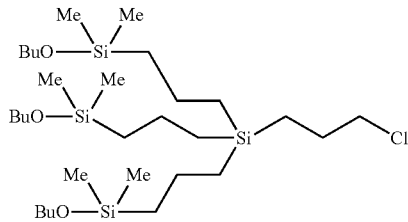 |
| 1-43 | 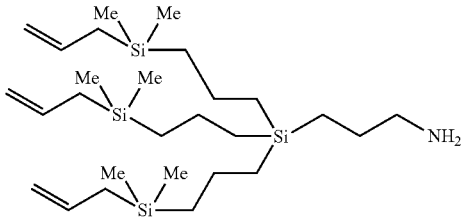 [SMILES: C=CC[Si](C)(C)CCC[Si](CCCN)(CCC[Si](C)(C)CC=C)CCC[Si](C)(C)CC=C] |
| 1-44 | 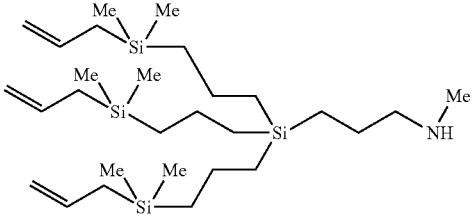 [SMILES: C=CC[Si](C)(C)CCC[Si](CCCNC)(CCC[Si](C)(C)CC=C)CCC[Si](C)(C)CC=C] |
| 1-45 | 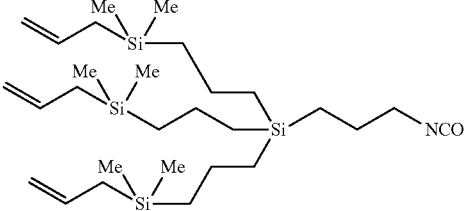 |

TABLE 1-continued

| No. | Organosilicon compound |
|---|---|
| 1-46 | (structure) |
| 1-47 | (structure) |
| 1-48 | (structure) |
| 1-49 | (structure) |
| 1-50 | (structure) |
| 1-51 | (structure) |
| 1-52 | (structure) |

Of the organosilicon compounds described in Table 1 above, compounds of Nos. 1-33 to 42 are particularly preferred. Those organosilicon compounds have three substituents having a group containing reactive silicon at a molecular end, and therefore can be bonded (fixed) to a surface of an inorganic oxide material at three points. Furthermore, those organosilicon compounds can be fixed to an inorganic oxide material at higher concentration than other organosilicon compounds. Furthermore, with those organosilicon compounds, bromine or chlorine in the organosilicon compound can be easily substituted with amine, phosphine or the like after fixing the compounds to a surface of the inorganic oxide material.

The organosilicon compound can be synthesized using the commercially available organosilane compound as a starting material and through Grinard reaction, hydrosilylation reaction, coupling reaction or the like. The starting material can be selected arbitrary. Haloalkylhalosilane or the like is easily available and is preferred as the starting material. Reactive silicon-containing group is constituted by the conventional technique such as Grinard reaction, hydrosilylation reaction or the like using haloalkylhalosilane or the like as a starting material, and a precursor of the organosilicon compound of the present application can be synthesized. The organosilicon compound of the present application can be obtained from the precursor of the organosilicon compound by introducing a substituent having an ability to support a transition metal or a compound thereof at a molecular end by the conventional technique such as coupling reaction or various addition reactions. The synthesis method of the organosilicon compound of the present application is described below in more detail, but it should not be construed thereto.

First, alkenyl Grinard is reacted with haloalkylhalosilane or the like to obtain haloalkyl(haloalkenyl)silane. The alkenyl Grinard used in the reaction includes the commercially available Grinard reagent and a compound prepared by reacting magnesium with any halide. Any organic solvent can be used as solvent, but ethers are preferably used due to its ease of synthesis and the like. If necessary, a dehydration solvent can be used. Ratio between the solvent and the haloalkylhalosilane can optionally be selected. However, in view of the facts that yield may be decreased due to generation of heat where an amount of the solvent is small, and reaction requires much time where an amount of the solvent is large, the ratio is preferably 1:1 to 1,000:1 in volume ratio. Amount of the Grinard reagent contained is an equimolar amount or more to a halogen bonded to silicon of the haloalkylhalosilane. Reaction can be conducted at room temperature, and may be conducted under heating.

Next, the haloalkyl(haloalkenyl) silane is hydrosilylated with alkoxyhydrosilane or halohydrosilane to obtain haloalkylsilyl alkylsilane. This compound may be used as an organosilicon compound precursor, and in the case that an end is halosilane, allyl Grinard, alcohol, imidazole or the like may further be acted, thereby deriving into a desired organosilicon compound precursor. Furthermore, haloalkyl group may be converted into a form suitable for introducing a metal coordination portion according to need. The hydrosilylation reaction may use a radical initiator, and may use a noble metal catalyst such as platinum or iridium. Those radical initiators or noble metal catalysts may be added in any amount so long as a reaction proceeds. Preferably, the ratio between the haloalkyl(haloalkenyl)silane and the radical initiator or noble metal catalyst is 1,000:1 to 1:10 in molar ratio. Furthermore, as the solvent, any organic solvent in which haloalkyl(haloalkenyl)silane, alkoxyhydrosilane, halohydrosilane and the like dissolve can be used. If necessary, a dehydration solvent can be used. The ratio between the solvent and the haloalkyl(haloalkenyl)silane can optionally be selected. However, where the amount of a solvent is small, yield may be decreased due to generation of heat, and where the amount of a solvent is large, much time is required for reaction. Therefore, the ratio is preferably 1:1 to 1,000:1 in volume ratio. The alkoxyhydrosilane or halohydrosilane is contained in equimolar amount or more to the haloalkyl(haloalkenyl)silane. The reaction can be conducted at room temperature, and may be conducted under heating.

Thereafter, an alkali metal salt such as a heteroelement compound is acted to the organosilicon compound precursor to perform a coupling reaction. Thus, various organosilicon compounds of the present application can be obtained. As the solvent, any organic solvent in which the organosilicon compound precursor, an alkali metal salt of a heteroelement compound and the like dissolve can be used. If necessary, a dehydration solvent can be used. The ratio between the solvent and the organosilicon compound precursor can optionally be selected. However, where the amount of a solvent is small, yield may be decreased due to generation of heat, and where the amount of a solvent is large, much time is required for reaction. Therefore, the ratio is preferably 1:1 to 1,000:1 in volume ratio. The alkali metal salt of a heteroelement compound is contained in equimolar amount or more to the organosilicon compound precursor. The reaction can be conducted at room temperature, and may be conducted under heating. The organosilicon compound obtained may be used as it is, and may be purified with a means such as silica gel column chromatography.

The inorganic oxide material which is another raw material of the composite material of the invention is not particularly limited and any material can be used so long as it is an inorganic oxide material conventionally used in a solid catalyst of this kind. Examples of the inorganic oxide material include single oxides of titanium, silicon, aluminum, zirconium and magnesium, and composite oxides containing those. More specifically, the examples include oxides such as silica, alumina, magnesia, titania and zirconia; composite oxides such as aluminosilicate and titanosilicate; regular mesoporous bodies such as MCM-41, SBA-15 and FSM-16; zeolites such as crystalline aluminosilicate, metallosilicate, aluminophosphate and silica aluminophosphate; mesoporous bodies; porous glasses; clay minerals; and mixtures thereof. Of those, titania, silica, alumina, zirconia and their composite oxides are preferred, and metal oxides containing silicon, such as silica, zeolite, mesoporous silica, porous glass, silica alumina and silica aluminophosphate, are particularly preferred. In any event, it is desired that an oxygen atom capable of bonding to an organosilicon compound is present on the surface of the inorganic oxide material.

The inorganic oxide material has an average pore size of preferably 0.5 to 500 nm, and more preferably 1 to 100 nm. To bond the organosilicon compound to the inorganic oxide material at high concentration, the inorganic oxide material preferably is porous and has a large surface area. For example, the inorganic oxide material having a specific surface area of 100 to 1,500 $m^2/g$ is preferred. The specific surface area can be calculated by, for example, BET method.

To bond the organosilicon compound to the inorganic oxide material through silicon atom of a reactive silicon-containing group of the organosilicon compound, the inorganic oxide material and the organosilicon compound are mixed in a solvent. For the solvent used in mixing, various solvents alone or mixtures thereof may be used. The solvent includes organic solvents, for example, aromatic hydrocarbons such as toluene and xylene; aliphatic saturated hydrocarbons such as pentane and hexane; and alcohols such as methanol and ethanol. In this case, the ratio between the solvent and the inorganic oxide material can optionally be selected. However, where the amount of the solvent is too small, the inorganic oxide material and the organosilicon compound are difficult to be mixed with each other, and where the amount of the solvent is too large, the concentration of the organosilicon compound in the solvent becomes dilute, and as a result, much time is required for bonding. For this reason, the ratio between the solvent and the inorganic oxide material is preferably 1:10 to 100:1 in volume ratio. The ratio between the organosilicon compound and the inorganic oxide material can optionally be selected. However, where the amount of the organosilicon compound is too small, the concentration of the organosilicon compound on the organic inorganic composite material becomes dilute, and where the amount is too large, the amount of the organosilicon compound which cannot bond to the surface of the inorganic oxide material is increased. For this reason, the ratio is preferably 1:1,000 to 100:1 in volume ratio. Mixing can be conducted at room temperature, but may be conducted under heating.

The composite material of the invention thus obtained is strongly bonded to the surface of the inorganic oxide material through silicon atoms of at least two groups containing reactive silicon at a molecular end, bonded to the organosilicon compound.

Specific examples of the organic inorganic composite material are shown below.

TABLE 2

| No. | Organic inorganic composite Material |
|---|---|
| 2-1 | |
| 2-2 | |
| 2-3 | |
| 2-4 | |

TABLE 2-continued
| No. | Organic inorganic composite Material |
|---|---|
| 2-5 | 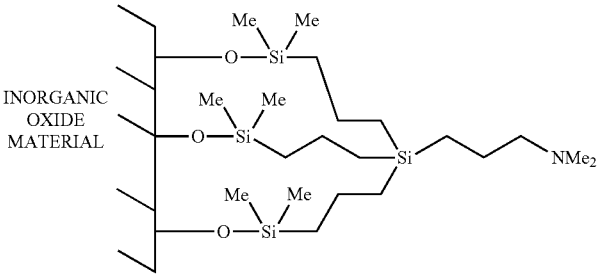 [SMILES: CCC1O[Si](C)(C)CCC[Si]2(CCCN(C)C)CCC[Si](C)(C)OC(CC)C1(C)O[Si](C)(C)CCC2] |
| 2-6 | 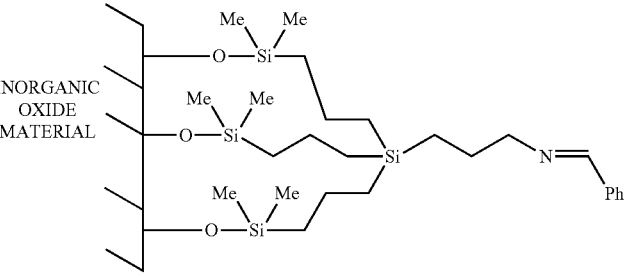 |
| 2-7 | 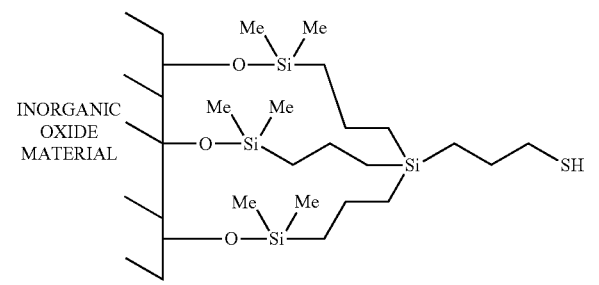 [SMILES: CCC1O[Si](C)(C)CCC[Si]2(CCCS)CCC[Si](C)(C)OC(CC)C1(C)O[Si](C)(C)CCC2] |
| 2-8 | 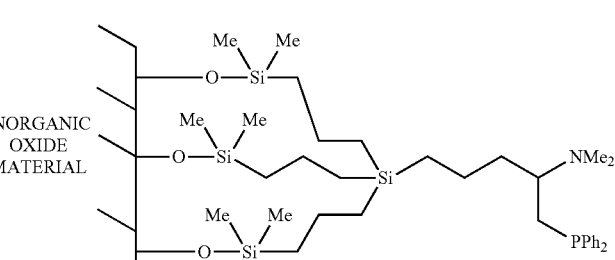 |
| 2-9 | 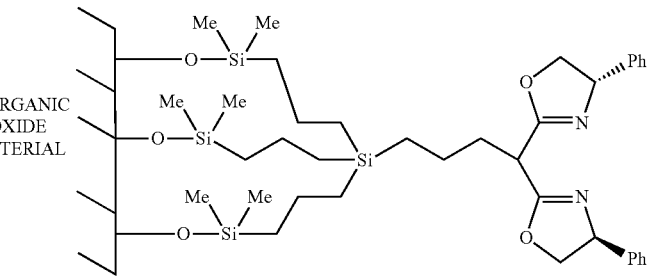 |

| No. | Organic inorganic composite Material |
|---|---|
| 2-10 | 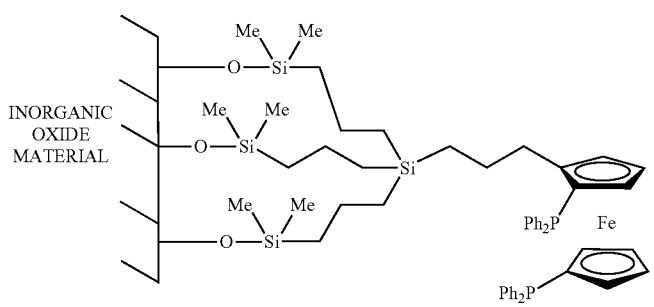 |
| 2-11 | 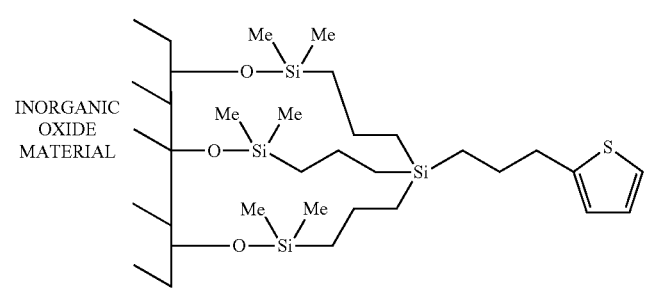 [SMILES: CCC1O[Si](C)(C)CCC[Si]2(CCCc3cccs3)CCC[Si](C)(C)OC(CC)C1(C)O[Si](C)(C)CCC2] |
| 2-12 | 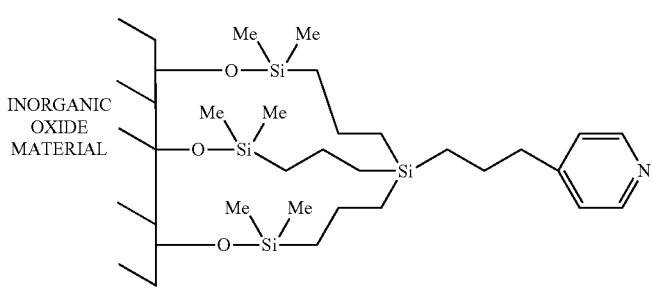 [SMILES: CCC1O[Si](C)(C)CCC[Si]2(CCCc3ccncc3)CCC[Si](C)(C)OC(CC)C1(C)O[Si](C)(C)CCC2] |
| 2-13 | 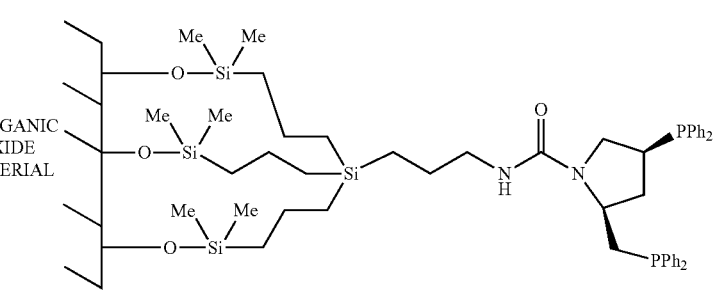 |
| 2-14 | 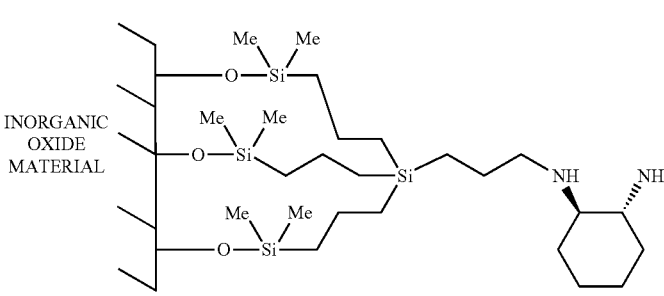 [SMILES: CCC1O[Si](C)(C)CCC[Si]2(CCCN[C@@H]3CCCC[C@H]3N)CCC[Si](C)(C)OC(CC)C1(C)O[Si](C)(C)CCC2] |

TABLE 2-continued

| No. | Organic inorganic composite Material |
|---|---|
| 2-15 | (structure) |
| 2-16 | (structure) |
| 2-17 | (structure) |
| 2-18 | (structure) |
| 2-19 | (structure) |

TABLE 2-continued

| No. | Organic inorganic composite Material |
|---|---|
| 2-20 | Inorganic oxide material with three O–Si(Me)₂–CH₂CH₂CH₂– linkages to a central Si bearing –CH₂CH₂CH₂Cl |
| 2-21 | Inorganic oxide material with three O–Si(Me)₂–CH₂CH₂CH₂– linkages to a central Si bearing –CH₂CH₂CH₂NH₂ |
| 2-22 | Inorganic oxide material with three O–Si(Me)₂–CH₂CH₂CH₂– linkages to a central Si bearing –CH₂CH₂CH₂NHMe |
| 2-23 | Inorganic oxide material with three O–Si(Me)₂–CH₂CH₂CH₂– linkages to a central Si bearing –CH₂CH₂CH₂NCO |
| 2-24 | Inorganic oxide material with three O–Si(Me)₂–CH₂CH₂CH₂– linkages to a central Si bearing –CH₂CH₂CH₂OH |

TABLE 2-continued

| No. | Organic inorganic composite Material |
|---|---|
| 2-25 | (structure: inorganic oxide material linked via three O–Si(Me)(Me)–(CH$_2$)$_3$– tethers to a central Si bearing –(CH$_2$)$_3$PPh$_2$ and an allyl group) |
| 2-26 | (structure: inorganic oxide material linked via two O–Si(Me)(Me)–(CH$_2$)$_3$– tethers to a central Si(Me) bearing –(CH$_2$)$_3$PPh$_2$) |
| 2-27 | (structure: inorganic oxide material linked via three (O)(O)Si(Me)–(CH$_2$)$_3$– tethers to a central Si bearing –(CH$_2$)$_3$PPh$_2$) |
| 2-28 | (structure: inorganic oxide material linked via two (O)(O)Si(Me)–(CH$_2$)$_3$– tethers to a central Si(Me) bearing –(CH$_2$)$_3$PPh$_2$) |
| 2-29 | (structure: inorganic oxide material linked via three (O)(O)(O)Si–(CH$_2$)$_3$– tethers to a central Si bearing –(CH$_2$)$_3$PPh$_2$) |

TABLE 2-continued

| No. | Organic inorganic composite Material |
|---|---|
| 2-30 | |
| 2-31 | |
| 2-32 | |
| 2-33 | |

TABLE 2-continued

| No. | Organic inorganic composite Material |
|---|---|
| 2-34 | 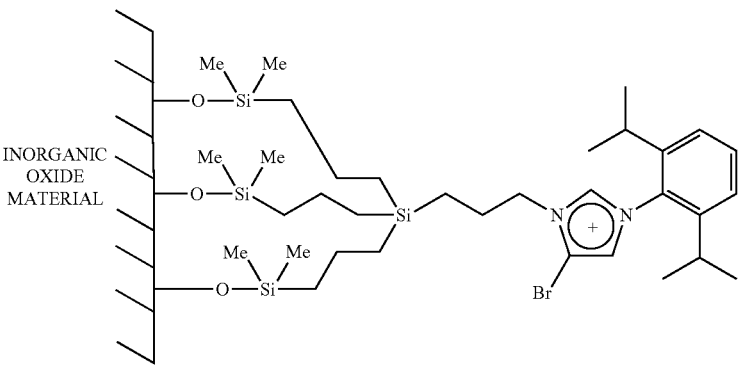 |

Of the organic inorganic composite materials described in Table 2 above, composite materials in which three substituents having a group containing reactive silicon at a molecular end of the organosilicon compound are bonded (fixed) to the inorganic oxide material at three points are particularly preferred. With the bonding at three points, an organic inorganic composite material comprising an organosilicon compound and an inorganic oxide material, bonded to each other at high concentration and strongly can be obtained, and the composite material having high ability of supporting a transition metal and the like can be provided. In this case, when the organosilicon compound has one substituent having an ability of supporting a transition metal or a compound thereof at a molecular end, an ability of supporting a transition metal and the like is further increased, which is preferred.

The composite material of the invention described hereinabove is useful in various uses of organic inorganic materials requiring strong bond between an organic material and an inorganic material, for example, catalysts, catalyst precursors, trapping agents for metal species and gels for separation. It is particularly preferred that the composite material is combined with a transition metal or a compound thereof to form an organic inorganic composite catalyst (hereinafter referred to as a "catalyst of the invention").

The catalyst of the invention comprises the composite material of the invention having supported thereon a transition metal or a compound thereof by a means such as coordination. In the catalyst of the invention, it is not necessary that all of the transition metal or a compound thereof is supported on the organosilicon compound constituting the composite material of the invention. For example, a transition metal or a compound thereof may be supported on the organosilicon compound itself, between the adjacent organosilicon compounds, between the organosilicon compound and the inorganic oxide material, and on the inorganic oxide material itself. Specifically, a method of supporting a transition metal or compound thereof includes a method of mixing a transition metal or a compound thereof with the composite material of the invention obtained above in a solvent and conducting a reaction; a method of previously bonding a transition metal or a compound thereof to a substituent having an ability of coordinating to the transition metal, of an organosilicon compound by mixing in a solvent, and bonding the same to an inorganic oxide material; and a method of previously fixing a transition metal or a compound thereof to an inorganic oxide material, and bonding an organosilicon compound to the same. In the catalyst of the invention, the ratio between the composite material of the invention and a transition metal or a compound thereof can optionally be selected, but the ratio is preferably 1:100 to 10,000:1 in weight ratio. The solvent used can optionally be selected from solvents capable of dissolving a transition metal compound to be bonded.

The transition metal or a compound thereof used in the catalyst of the invention is not particularly limited so long as it has catalytic activity, and examples thereof include salts of transition metals, homo or hetero dinuclear complexes, single metal and cluster. The transition metal or a compound thereof may have an organic substituent and a ligand. Specifically, as metal species of a transition metal, late transition metals are preferred, and for example, transition metals of Group 8 and noble metals are preferred. Examples of such metal species specifically include ruthenium, cobalt, rhodium, iridium, nickel, palladium, platinum and gold.

The catalyst of the invention can be utilized as a catalyst of various reactions. The catalyst is effective as a catalyst for a coupling reaction such as homo-coupling or cross-coupling; for an addition reaction such as hydrosilylation, carbonylation, hydroformylation, Michael addition or hydrogenation (including asymmetric hydrogenation); and the like, and is particularly effective as a catalyst for a cross-coupling reaction or a hydrogenation reaction.

Of the above reactions, the cross-coupling reaction differs from a homo-coupling reaction which bonds the two same chemical species, and is a reaction which selectively bonds two different chemical species. Furthermore, the cross-coupling reaction is a reaction which proceeds by using a transition metal as a catalyst. In the case that the catalyst is used in a cross-coupling reaction, the transition metal or a compound thereof is preferably platinum, palladium or nickel.

Representative examples of the cross-coupling reaction include the following reactions. The catalyst of the invention is effective to any of those cross-coupling reactions.

(1) Suzuki Coupling Reaction

A reaction of cross-coupling an organoboron compound, an organohalide and the like under a basic condition using a transition metal such as palladium as a catalyst.

(2) Mizoroki-Heck Coupling Reaction

A reaction of synthesizing an alkenyl aryl compound by cross-coupling a terminal alkene and a halogenated aryl under a basic condition using a transition metal such as palladium as a catalyst.

(3) Negishi Coupling Reaction

A reaction of cross-coupling an organozinc compound, an organohalide, and the like using a transition metal such as palladium or nickel as a catalyst.

(4) Stille Coupling Reaction

A reaction of cross-coupling an organotin compound and an organohalide using a transition metal such as palladium as a catalyst.

(5) Tsuji-Trost Coupling Reaction

A reaction of synthesizing an allyl-position alkylated product by cross-coupling an allyl ester and an organonucleophile under a basic condition using a transition metal such as palladium as a catalyst.

(6) Sonogashira Coupling Reaction

A reaction of synthesizing an alkynyl aryl compound by cross-coupling a terminal alkyne, halogenated aryl and the like under a basic condition using a transition metal such as palladium as a catalyst.

(7) Kumada-Tamao Coupling Reaction

A reaction of cross-coupling a Grinard reagent and an organohalide using a transition metal such as nickel or palladium as a catalyst.

(8) Buchwald-Hartwig Coupling Reaction

A reaction of synthesizing aryl amine or aryl ether by cross-coupling halogenated aryl and amine or alcohol under a basic condition using a transition metal such as palladium as a catalyst.

One preferred embodiment of the cross-coupling reaction using the catalyst of the invention is described below by reference to Suzuki coupling reaction. Raw materials used in the synthesis of a biaryl compound by Suzuki coupling reaction include halogenated aryl and aryl boronic acid. The respective raw materials may be substituted with various substituents on an aryl group. A compound containing platinum, palladium or nickel is preferably used as the transition metal compound of the catalyst of the invention used in the present reaction.

The base concurrently present in a cross-coupling reaction system includes both organic base and inorganic base. Inorganic base is preferred. Specific examples of the inorganic base include sodium hydroxide, potassium hydroxide, cesium hydroxide, sodium carbonate, potassium carbonate, cesium carbonate, sodium phosphate, potassium phosphate and sodium acetate.

In the case of practicing a cross-coupling reaction, a solvent is not always necessary, but various solvents may be used alone or as mixtures thereof. Examples of the solvent include organic solvents, for example, aromatic hydrocarbons such as toluene and xylene, ethers such as diethyl ether, dibutyl ether and tetrahydrofuran, aliphatic saturated hydrocarbons such as pentane and hexane, and alcohols such as methanol and ethanol; and water.

Separation of the catalyst of the invention after a cross-coupling reaction is conducted by filtration and the like. Therefore, the catalyst separated can directly be reutilized as a catalyst of the cross-coupling reaction. Separation of a product after the cross-coupling reaction can easily be performed by a general purification isolation method such as distillation/recrystallization after removing the catalyst of the invention by filtration and the like.

On the other hand, of the above reactions, the hydrogenation reaction is a reduction reaction which adds hydrogen atom to a compound by a reducing agent.

One preferred embodiment of the hydrogenation reaction using the catalyst of the invention is described below. A raw material used in the hydrogenation reaction includes a compound having an unsaturated bond in the molecule. Furthermore, ruthenium, cobalt, rhodium, iridium, nickel, palladium, platinum, gold or compounds containing those are preferably used as the transition metal or a compound thereof of the catalyst of the invention used in the present reaction.

In the case of practicing the hydrogenation reaction, a solvent is not always necessary, but various solvents may be used alone or as mixtures thereof. In the case of using a solvent, examples of the solvent include organic solvents, for example, aromatic hydrocarbons such as toluene and xylene, ethers such as diethyl ether, dibutyl ether and tetrahydrofuran, aliphatic saturated hydrocarbons such as pentane and hexane, and alcohols such as methanol and ethanol; and water.

Separation of the catalyst of the invention after the hydrogenation reaction is conducted by filtration and the like. Therefore, the catalyst separated can directly be reutilized as a catalyst of the hydrogenation reaction. Separation of a product after the hydrogenation reaction can easily be performed by a general purification isolation method such as distillation/recrystallization after removing the catalyst by filtration and the like.

EXAMPLES

The present invention is described in detailed below by reference to examples, but the invention is not limited by those examples.

Example 1

Synthesis (1) of Organosilicon Compound 14.0 g (54.6 mmol) of 3-bromopropyltrichlorosilane (compound I) and 82 ml (containing 163.8 mmol of allyl magnesium chloride) of an allyl magnesium chloride THF solution were reacted in 280 ml of THF at room temperature for 5 hours. After the reaction, water-soluble salts were removed, followed by drying and distillation. Thus, 11.2 g of 3-bromopropyltriallylsilane (compound II) as the objective compound was obtained.

Br~~~SiCl₃ ⟶

(Compound I)

Br~~~Si(~~)₃

(Compound II)

0.3 g (1.1 mmol) of the 3-bromopropyltriallylsilane (compound II) obtained above, 0.34 g (3.6 mmol) of dimethylchlorosilane, 16.2 mg (0.024 mmol) of chloro-1,5-cyclooctadiene iridium dimer and 11.9 mg (0.11 mmol) of 1,5-cyclooctadiene were reacted in 1.2 ml of toluene at 60° C. for 1 hour. After the reaction, the reaction mixture was cooled to room temperature, and a solvent was distilled away under reduced pressure. 0.57 ml (containing 1.1 mmol of allyl magnesium chloride) of allyl magnesium chloride THF solution was reacted with the reaction mixture in THF at room temperature for 1 hour. Thus, 0.66 g of compound III was obtained.

Br~~~Si(~~)₃ ⟶

(Compound II)

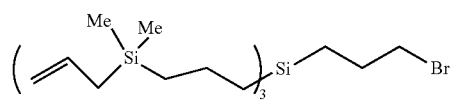

(Compound III: corresponding to No. 1-52 in Table 1))

0.3 g (0.5 mmol) of the compound III and 1.3 ml (containing 0.63 mmol of potassium diphenyl phosphide) of potassium diphenyl phosphide THF solution were reacted in 5 ml of THF for 17.5 hours. After the reaction, insoluble matters were filtered off, and a solvent was distilled away under reduced pressure. The reaction mixture was further purified with silica gel column chromatography (hexane/ethyl acetate=100/1). Thus, 0.34 g of compound IV as an organosilicon compound was obtained. NMR was measured on the compound IV. The results are shown below.

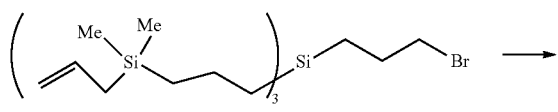

(Compound III)

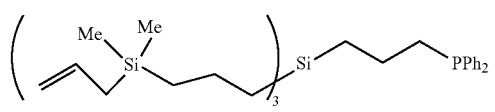

(Compound IV: corresponding to No. 1-1 in Table 1)

$^1$H NMR ($C_6D_5CD_3$, δ):

0.02 (s, 18H), 0.61-0.68 (m, 12H), 0.78-0.88 (m, 2H), 1.40-1.52 (m, 12H), 2.05-2.09 (m, 4H), 4.92 (d, J=15.9 Hz, 6H), 5.74-5.83 (m, 3H), 7.0-7.14 (m, 6H), 7.42 (t, J=6.1 Hz, 4H).

Example 2

Synthesis (2) of Organosilicon Compound 1.93 g (3.36 mmol) of the compound III synthesized in Example 1 above, 0.68 g (8.38 mmol) of calcium cyanate and 0.13 g (0.78 mmol) of potassium iodide were heated at 100° C. in 5 ml of DMF to conduct a reaction for 2 hours. After the reaction, the resulting reaction solution was cooled to room temperature. 10 ml of hexane was added to the reaction solution, and after filtering off insoluble matters, a solvent was then distilled away under reduced pressure. Thus, 1.53 g of compound V as an organosilicon compound was obtained. NMR was measured on the compound V. The results are shown below.

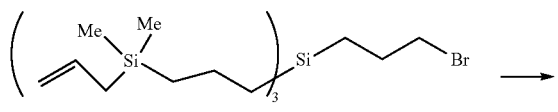

(Compound III)

(Compound V: corresponding to No. 1-45 in Table 1)

$^1$H NMR ($CDCL_3$, δ):

−0.03 (s, 18H), 0.48-0.59 (m, 14H), 1.26-1.34 (m, 8H), 1.48 (d, J=8.1 Hz, 6H), 3.23 (t, J=6.7 Hz, 1H), 4.80 (d, J=7.9 Hz, 3H), 4.81 (d, J=17.8 Hz, 3H), 5.76 (ddt, J=17.8, 7.9, 6.7 Hz, 3H)

0.71 g (1.49 mmol) of the compound V and 0.50 g (1.10 mmol) of (2S,4S)-4-(diphenylphosphino)-2-[(diphenylphosphino)-methyl]pyrrolidine were reacted in 10 ml of methylene chloride at room temperature for 15 hours. After the reaction, a solvent was distilled away under reduced pressure. The reaction mixture was further purified with silica gel column chromatography (hexane/ethyl acetate=4/1). Thus, 0.36 g of compound VI as an organosilicon compound was obtained. NMR was measured on the compound VI. The results are shown below.

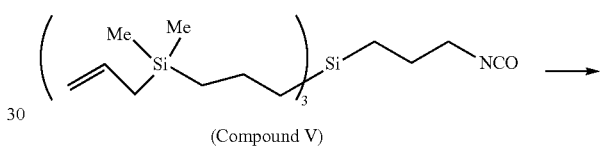

(Compound V)

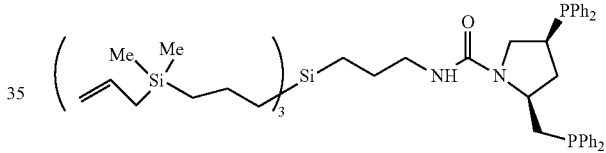

(Compound VI: corresponding to No. 1-15 in Table 1)

$^1$H NMR ($CDCL_3$, δ):

−0.05 (s, 18H), 0.48-0.59 (m, 14H), 1.23-1.31 (m, 8H), 1.48 (d, J=8.1 Hz, 6H), 1.60 (br, 1H), 2.12 (dd, J=11.9, 10.7 Hz, 1H), 2.27-2.29 (m, 1H), 2.79-2.82 (m, 1H), 3.01-3.06 (m, 3H), 3.18 (q, J=9.8 Hz, 1H), 3.53 (br, 1H), 3.85-3.94 (m, 2H), 4.79 (d, J=9.2 Hz, 3H), 4.80 (d, J=17.3 Hz, 3H), 5.73 (ddt, J=17.3, 9.2, 8.1 Hz, 3H), 7.24-7.39 (m, 16H), 7.41-7.45 (m, 2H), 7.52-7.56 (m, 2H)

Example 3

Preparation of Organic Inorganic Composite Material 0.45 g (0.78 mmol) of the compound III was refluxed together with 2.1 g of a silica powder (BET specific surface area: 1,039 m$^2$/g, average pore size: 4 nm) in heptane for 48 hours in an argon atmosphere, followed by filtration, washing and drying under reduced pressure at 80° C. Thus, an organic inorganic composite material corresponding to No. 2-19 in Table 2 (hereinafter referred to as "organic inorganic composite material 2-19") was obtained. An amount of fixed ligand in the organic inorganic composite material 2-19 obtained by an elemental analysis was 0.33 mmol/g. $^{29}$Si CP-MAS NMR spectrum analysis was conducted on the organic inorganic composite material 2-19 obtained. The results are shown in FIG. 1. It was seen that the organic inorganic composite material 2-19 obtained had a silicon compound and silica gel strongly fixed to each other at three points.

Example 4

Preparation of Organic Inorganic Composite Material 0.23 g of tris[(dimethylallylsilyl)propyl]diphenyl-phosphinopropylsilane (corresponding to No. 1-1 in Table 1) of the compound IV was refluxed together with 3.5 g of a silica powder (BET specific surface area: 1,039 m²/g, average pore size: 4 nm) in toluene for 88 hours in an argon atmosphere, followed by filtration, washing and drying under reduced pressure at 80° C. Thus, an organic inorganic composite material corresponding to No. 2-25 in Table 2 (hereinafter referred to as "organic inorganic composite material 2-25") was obtained. An amount of fixed ligand in the organic inorganic composite material 2-25 obtained by an elemental analysis was 0.07 mmol/g. ²⁹Si CP-MAS NMR spectrum analysis was conducted on the organic inorganic composite material 2-25 obtained. The results are shown in FIG. 2. It was seen that the organic inorganic composite material 2-25 obtained had a silicon compound and silica gel strongly fixed to each other at two points.

Example 5

Preparation of Catalyst for Suzuki Coupling Reaction 1 g of the organic inorganic composite material 2-25 having a ligand fixed thereto prepared in Example 4 above and 2.6 mg of palladium acetate were stirred in THF at room temperature for 24 hours. Thereafter, filtration, washing and drying under reduced pressure at 80° C. were conducted. Thus, organic inorganic composite catalyst 1 was obtained. As a result of quantifying Pd in a filtrate generated in the preparation of the organic inorganic composite catalyst 1, the quantity was smaller than the lower limit of analysis.

Example 6

Suzuki Coupling Reaction

Suzuki coupling reaction was conducted using the organic inorganic composite catalyst 1 obtained in Example 5 above. Specifically, 1 ml of p-bromobenzoic acid, 846 mg (1.1 times per mole of p-bromobenzoic acid) of phenylboronic acid, 1,692 mg (2 times per mole of p-bromobenzoic acid) of potassium carbonate, 1 ml of p-tert-butyltoluene as an internal standard substance and 250 mg (0.05 mol % in terms of Pd to p-bromobenzoic acid) of the organic inorganic composite catalyst 1 obtained in Example 5 above were stirred in 6 ml of toluene at 100° C. for 5 hours. As a result of determining yield of ethyl biphenyl benzoate with gas chromatography, it was found to be 84%. An amount of Pd eluted in a product in this case was smaller than the lower limit of detection.

Example 7

Synthesis (3) of Organosilicon Compound 6.0 g (21.8 mmol) of 3-bromopropyltriallylsilane (compound II), 0.34 g (3.6 mmol) of dimethylchlorosilane, 16.2 mg (0.024 mmol) of chloro-1,5-cyclooctadiene iridium dimer and 11.9 mg (0.11 mmol) of 1,5-cyclooctadiene were reacted in 1.2 ml of toluene at 60° C. for 1 hour. After the reaction, the resulting reaction mixture was cooled to room temperature, and a solvent was distilled away under reduced pressure. The reaction mixture was dissolved in 80 ml of diethyl ether, and ml of isopropyl alcohol was added thereto. 18 ml of triethyl amine was added dropwise to the mixture, followed by stirring at room temperature for 18 hours. A salt precipitated was filtered off, and a solvent was distilled away under reduced pressure. Purification was conducted with silica gel column chromatography (hexane/ethyl acetate=100/1). Thus, 12.0 g of compound VII was obtained.

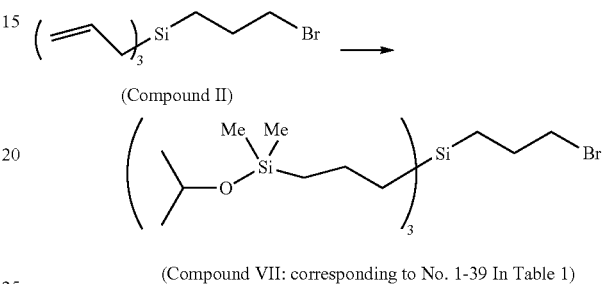

(Compound VII: corresponding to No. 1-39 In Table 1)

¹H NMR (CDCl₃, δ):
0.05 (s, 18H), 0.49-0.64 (m, 14H), 1.11 (d, J=6.2 Hz, 18H), 1.26-1.40 (m, 6H), 1.75-1.83 (m, 2H), 3.34 (t, J=7.0 Hz, 2H), 3.94 (sept, J=6.2 Hz, 3H)

Example 8

Synthesis (4) of Organosilicon Compound 1.20 g (3.36 mmol) of the compound VII, 0.68 g (8.38 mmol) of calcium cyanate and 0.13 g (0.78 mmol) of potassium iodide were heated in 5 ml of DMF at 100° C. to conduct a reaction for 2 hours. After the reaction, the resulting reaction solution was cooled to room temperature, and 10 ml of hexane was added to the reaction solution. Insoluble matters were filtered off, and a solvent was distilled away under reduced pressure. Thus, 1.53 g of compound VIII as an organosilicon compound was obtained. NMR was measured on the compound VIII. The results are shown below.

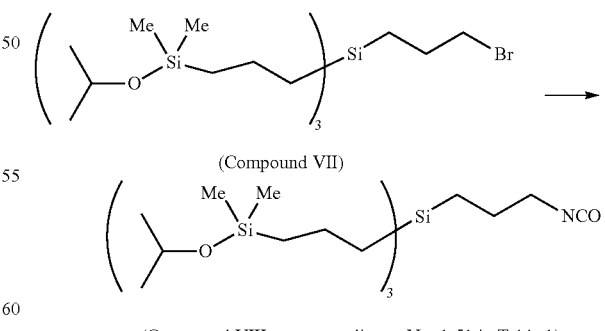

(Compound VIII: corresponding to No. 1-51 in Table 1)

¹H NMR (CDCl₃, δ):
0.06 (s, 18H), 0.49-0.64 (m, 14H), 1.11 (d, J=6.2 Hz, 18H), 1.26-1.40 (m, 6H), 1.75-1.83 (m, 2H), 3.21 (t, J=6.6 Hz, 2H), 3.96 (sept, J=6.2 Hz, 3H)

Example 9

Synthesis (5) of Organosilicon Compound 0.71 g (1.49 mmol) of the compound VIII and 0.50 g (1.10 mmol) of (2S,4S)-4-(diphenylphosphino)-2-[(diphenylphosphino)methyl]pyrrolidine were reacted in 10 ml of methylene chloride at room temperature for 15 hours. After the reaction, a solvent was distilled away under reduced pressure, and purification was conducted with silica gel column chromatography (hexane/ethyl acetate=4/1). Thus, 0.36 g of compound 1-32 as an organosilicon compound was obtained. NMR was measured on the compound IX. The results are shown below.

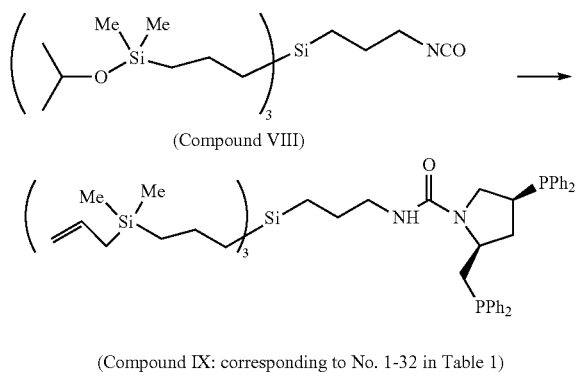

(Compound VIII)

(Compound IX: corresponding to No. 1-32 in Table 1)

$^1$H NMR (CDCL$_3$, δ):
0.11 (s, 18H), 0.48-0.59 (m, 14H), 1.06 (d, J=6.2 Hz) 1.23-1.31 (m, 8H), 1.60 (br, 1H), 2.27-2.29 (m, 1H), 2.79-2.82 (m, 1H), 3.01-3.06 (m, 3H), 3.18 (q, J=9.8 Hz, 1H), 3.53 (br, 1H), 3.71-3.83 (m, 2H), 3.91 (sept, J=6.2 Hz, 6H) 7.24-7.39 (m, 16H), 7.41-7.45 (m, 2H), 7.52-7.56 (m, 2H)

Example 10

Preparation of Catalyst for Hydrogenation Reaction 10 ml of a toluene solution of 0.13 g (0.13 mmol) of the compound VI was added to 0.7 g of a silica powder vacuum dried at 80° C. (BET specific surface area: 1,039 m$^2$/g, average pore size: 4 nm) at room temperature, and the resulting mixture was refluxed with heating for 72 hours. A solid obtained was washed with a solvent, and dried under reduced pressure at 80° C. Thus, an organic inorganic composite material corresponding to No. 2-13 in Table 2 (hereinafter referred to as "organic inorganic composite material 2-13") was obtained. The supported amount of the compound VI in the organic inorganic composite material 2-13 obtained by elemental analysis was 0.33 mmol/g.

Example 11

Asymmetric Hydrogenation Reaction

The organic inorganic composite material 2-13 (50 mg) and 2 mg (4.9 mmol) of bis(cyclooctadiene)rhodium (I) tetrafluoroborate were stirred in 3 ml of methanol at room temperature for 30 minutes in a hydrogen atmosphere of 1 atm. 105 mg (0.51 mmol) of α-(acetoamido)cinnamic acid was added to the resulting mixture, and reaction was conducted at room temperature for 30 minutes. Thus, N-acetyl-phenylalanine was obtained. An enantiomer excess of D-form determined by HPLC analysis (Chirace AD-H, manufactured by Daicel) was 97% e.e.

Example 12

Preparation of Organic Inorganic Composite Material 10 ml of a methanol solution (40%) of methylamine was added to the organic inorganic composite material 2-19 (1.0 g) prepared in Example 3. After conducting a reaction at 80° C. for 20 hours, a solid obtained was washed with a solvent, and dried under reduced pressure at 80° C. Thus, an organic inorganic composite material corresponding to No. 2-22 in Table 2 (hereinafter referred to as "organic inorganic composite material 2-22") was obtained.

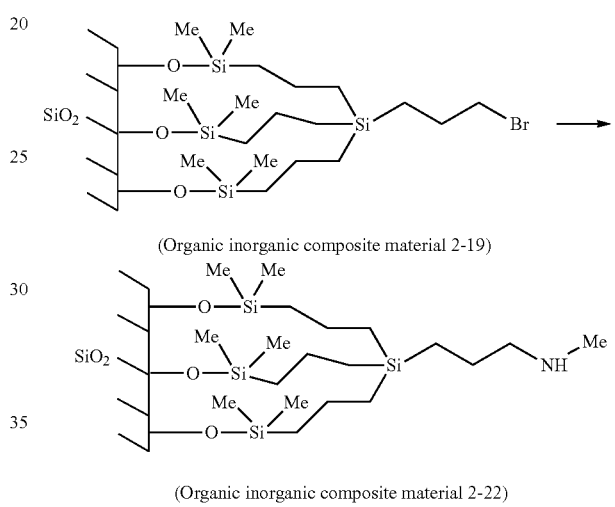

(Organic inorganic composite material 2-19)

(Organic inorganic composite material 2-22)

Example 13

Preparation of Catalyst for Suzuki Coupling Reaction 0.3 g of the organic inorganic composite material 2-22 having fixed thereto a ligand prepared in Example 12 above and 4.0 mg of palladium acetate were stirred in THF at room temperature for 24 hours. Thereafter, filtration and washing were conducted, and drying was conducted under reduced pressure at 80° C. Thus, an organic inorganic composite catalyst 2 was obtained. As a result of quantifying Pd in a filtrate generated in the preparation of the organic inorganic composite catalyst 2, the quantity was smaller than the lower limit of analysis.

Example 14

Suzuki Coupling Reaction

Suzuki coupling reaction was conducted using the organic inorganic composite catalyst 2 obtained in Example 13 above. Specifically, 1 ml of p-bromobenzoic acid, 846 mg (1.1 times per mole of p-bromobenzoic acid) of phenylboronic acid, 1,692 mg (2 times per mole of p-bromobenzoic acid) of potassium carbonate, 1 ml of p-tert-butyltoluene as an internal standard substance and 60 mg (0.05 mol % in terms of Pd to p-bromobenzoic acid) of the organic inorganic composite catalyst 2 obtained in Example 14 above were stirred in 6 ml of toluene at 100° C. for 1 hour. As a result of determining yield of ethyl biphenyl benzoate with gas chromatography, it was found to be 100%. An amount of Pd eluted in a product in this case was smaller than the lower limit of detection.

Example 15

Preparation of Organic Inorganic Composite Material

The organic inorganic composite material 2-19 (0.5 g) prepared in Example 3 and 30 ml of a THF solution (0.5 mol/L) of potassium diphenylphosphate were refluxed with heating in 30 ml of THF for 17 hours. A solid obtained was washed with a solvent, and dried under reduced pressure at 80° C. Thus, an organic inorganic composite material corresponding to No. 2-1 in Table 2 (hereinafter referred to as "organic inorganic composite material 2-1") was obtained.

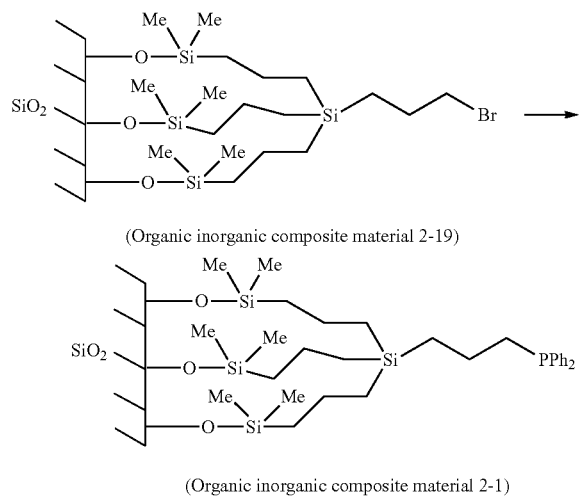

(Organic inorganic composite material 2-19)

(Organic inorganic composite material 2-1)

Example 16

Preparation of Catalyst for Suzuki Coupling Reaction 0.37 g of the organic inorganic composite material 2-1 having fixed thereto a ligand prepared in Example 15 above and 3.3 mg of palladium acetate were stirred in THF at room temperature for 24 hours, followed by filtration, washing and drying under reduced pressure at 80° C. Thus, an organic inorganic composite catalyst 3 was obtained. As a result of quantifying Pd in a filtrate generated in the preparation of the organic inorganic composite catalyst 3, the quantity was smaller than the lower limit of analysis.

Example 17

Suzuki Coupling Reaction

Suzuki coupling reaction was conducted using the organic inorganic composite catalyst 3 obtained in Example 16 above. Specifically, 1 ml of p-bromobenzoic acid, 846 mg (1.1 times per mole of p-bromobenzoic acid) of phenylboronic acid, 1,692 mg (2 times per mole of p-bromobenzoic acid) of potassium carbonate, 1 ml of p-tert-butyltoluene as an internal standard substance and 77 mg (0.05 mol % in terms of Pd to p-bromobenzoic acid) of the organic inorganic composite catalyst 3 obtained in Example 14 above were stirred in 6 ml of toluene at 100° C. for 5 hours. As a result of determining yield of ethyl biphenyl benzoate with gas chromatography, it was found to be 81%. An amount of Pd eluted in a product in this case was smaller than the lower limit of detection.

Example 18

Preparation of Organic Inorganic Composite Material 1.34 g of 1-(2,6-diisopropylphenyl)-1H-imidazole and 10 ml of toluene were added to the organic inorganic composite material 2-19 (1.0 g) prepared in Example 3. Reaction was conducted under reflux with heating for 4 days. A solid obtained was washed with a solvent, and dried under reduced pressure at 80° C. Thus, an organic inorganic composite material corresponding to No. 2-34 in Table 2 was obtained.

Comparative Example 1

Preparation of Comparative Organic Inorganic Composite Material A 0.16 g (0.81 mmol) of 3-chloropropyltrimethoxysilane was refluxed together with 2.1 g of a silica powder (BET specific surface area: 1,039 m$^2$/g, average pore size: 4 nm) in heptane for 48 hours in an argon atmosphere. Filtration, washing and drying under reduced pressure at 80° C. were then conducted. Thus, comparative organic inorganic composite material A was obtained. The amount of a fixed ligand in the comparative organic inorganic composite material A determined by elemental analysis was 1.23 mmol/g.

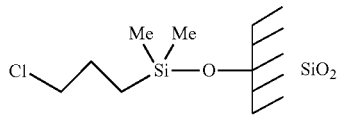

Comparative Example 2

Preparation of Comparative Organic Inorganic Composite Material B 0.16 g (0.91 mmol) of 3-chloropropyldimethyl methoxysilane was refluxed together with 2.1 g of a silica powder (BET specific surface area: 1,039 m$^2$/g, average pore size: 4 nm) in heptane for 48 hours in an argon atmosphere. Filtration, washing and drying under reduced pressure at 80° C. were then conducted. Thus, comparative organic inorganic composite material B was obtained. The amount of a fixed ligand in the comparative organic inorganic composite material B determined by elemental analysis was 1.19 mmol/g.

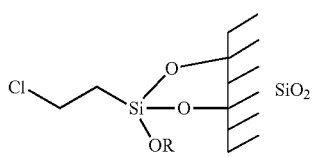

Test Example 1

Anti-Leaching Performance Evaluation of Organic Inorganic Composite Material The organic inorganic composite material 2-19 (0.1 g) prepared in Example 3 was stirred in water at 80° C. for 48 hours to conduct an endurance test. A residual amount of an organic substance is quantified by elemental analysis of the organic inorganic composite material after the endurance test, and leaching rate of organic components was determined from the difference in the amount of the organic substance before and after the endurance test. The results are shown in Table 3. The comparative organic inorganic composite material A prepared in Comparative Example 1 and the comparative organic inorganic composite material A prepared in Comparative Example 2 were subjected to an endurance test by the same method as above, and the leaching rate was determined. Those results are shown in Table 3.

TABLE 3

| | Organic inorganic composite material | Fixed amount | Amount of organic substance after endurance test | Leaching rate |
| --- | --- | --- | --- | --- |
| Example 3 | 2-19 | 0.33 mmol/g | 0.31 mmol/g | 7% |
| Comparative Example 1 | A | 1.23 mmol/g | 0.66 mmol/g | 51% |
| Comparative Example 2 | B | 1.19 mmol/g | 0.70 mmol/g | 46% |

From the above results, it was clarified that the organic inorganic composite material of the present invention has excellent anti-leaching performance as compared with the conventional materials.

INDUSTRIAL APPLICABILITY

The organic inorganic composite material of the present invention is useful in a catalyst, a catalyst precursor, a trapping agent of metal species, a gel for separation, and the like.

Furthermore, particularly when a transition metal compound is supported on the organic inorganic composite material by a means such as coordination, an organic inorganic composite catalyst exhibiting excellent anti-leaching performance can be formed. Additionally, the organic inorganic composite catalyst can easily be separated from a reaction liquid, and therefore can repeatedly be used in a reaction, which is economical.

Figure 1:
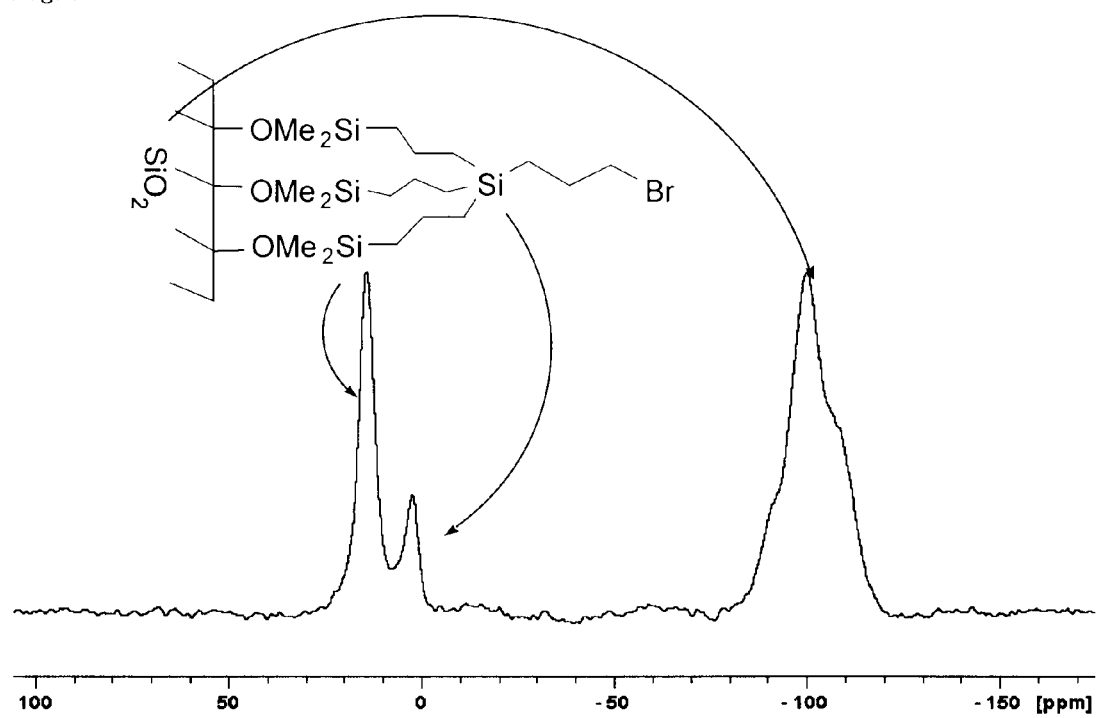
FIG. 1 is $^{29}$Si CP-MAS NMR spectrum of the organic inorganic composite material 2-19.
Figure 2:
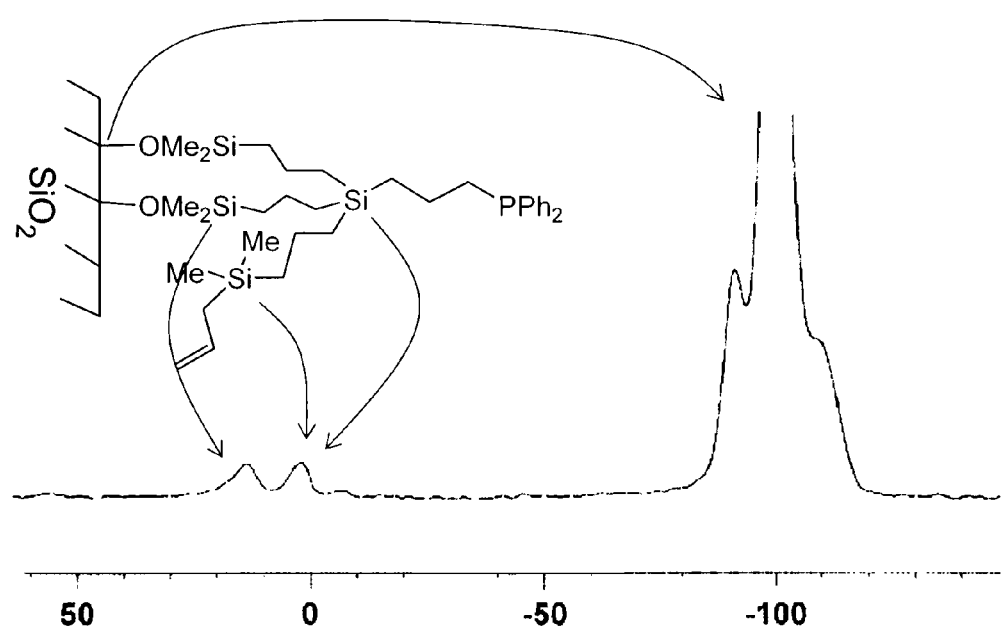
FIG. 2 is $^{29}$Si CP-MAS NMR spectrum of the organic inorganic composite material 2-25.

The invention claimed is:

1. An organic inorganic composite catalyst comprising an organic inorganic composite material and palladium,
   wherein the organic inorganic composite material comprises an organosilicon compound and an inorganic oxide material,
   wherein the organosilicon compound and the inorganic oxide material are bonded to each other through a plurality of groups containing reactive silicon of the organosilicon compound,
   wherein the organosilicon compound is represented by formula (1)

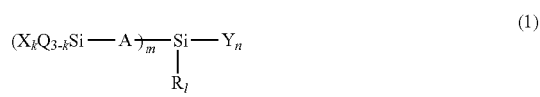

wherein X represents chlorine, bromine, iodine, a siloxy group, a hydroxy group, an alkoxy group, an allyl group or an imidazolyl group; Y provides for support of the palladium and represents a monovalent organic group containing at least one of a hydroxyl group, an alkoxy group, an aryloxy group, an isocyanato group, a mercapto group, a phosphino group, an amino group, an imino group, a halogen and a heterocyclic ring; A represents a linear alkylene group having 2 or more carbon atoms; R represents a methyl group, an ethyl group, a butyl group or a phenyl group; Q represents a methyl group, an ethyl group, a butyl group or a phenyl group; k is an integer of 1; n is an integer of 1 or 2; m is an integer of 2 or 3; l is an integer of 0 or 1; and l+m+n is 4; and
   wherein the organic inorganic composite material has palladium or a compound containing palladium supported thereon.

2. The organic inorganic composite catalyst according to claim 1, wherein an oxygen atom on a surface of the inorganic oxide material and a silicon atom of the organosilicon compound are covalent-bonded.

3. The organic inorganic composite catalyst according to claim 1, wherein the inorganic oxide material is a single oxide of titanium, silicon, aluminum, zirconium or magnesium, or a composite oxide containing titanium, silicon, aluminum, zirconium or magnesium.

4. The organic inorganic composite catalyst according to claim 1, wherein the organosilicon compound of formula (1) is represented by formula (2):

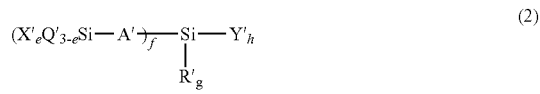

wherein X' represents chlorine, bromine, iodine, siloxy group, hydroxy group, alkoxy group, allyl group or imidazolyl group, Y' represents a monovalent organic group containing halogen, A' represents a linear alkylene group having 2 or more carbon atoms, R' represents methyl group, ethyl group, butyl group or phenyl group, Q' represents methyl group, ethyl group, butyl group or phenyl group, e is an integer of 1, f is 2 or 3, h is 1 or 2, g is 0 or 1, and f+h+g is 4.

5. The organic inorganic composite catalyst according to claim 1, wherein n is an integer of 1, m is an integer of 3 and l is zero.

6. The organic inorganic composite catalyst according to claim 4, wherein h is an integer of 1, f is an integer of 3 and g is zero.

* * * * *